Figure 1:
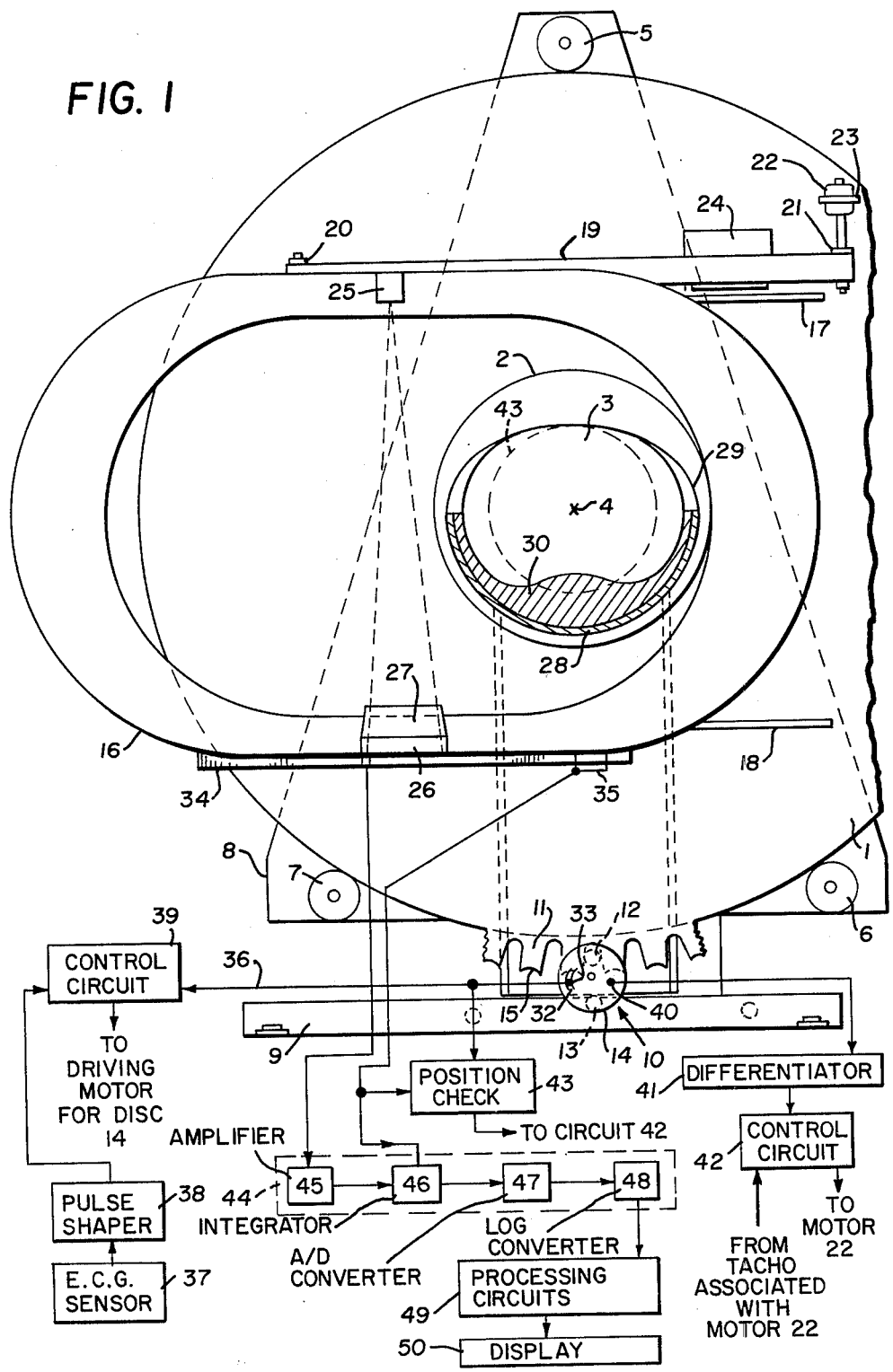

United States Patent [19]

Hounsfield et al.

[11] 4,206,363

[45] Jun. 3, 1980

[54] RADIOGRAPHY

[75] Inventors: Godfrey N. Hounsfield, Newark; Richard G. Gillard, Uxbridge, both of England

[73] Assignee: E M I Limited, Hayes, England

[21] Appl. No.: 924,041

[22] Filed: Jul. 12, 1978

[30] Foreign Application Priority Data

Jul. 15, 1977 [GB] United Kingdom ............... 29888/77

[51] Int. Cl.² ............................................ G03B 41/16
[52] U.S. Cl. .................................. 250/445 T; 250/402
[58] Field of Search ............................ 250/445 T, 402

[56] References Cited

U.S. PATENT DOCUMENTS 4,126,785  11/1978  Hounsfield ...................... 250/445 T Primary Examiner—Craig E. Church
Attorney, Agent, or Firm—Cooper, Dunham, Clark, Griffin & Moran

[57] ABSTRACT

Computerized tomographic apparatus is described in which a radiation source and an associated detector array execute, concomitantly, reciprocating lateral scanning movements and rotational scanning movements relative to a patient's body, the scanning movements being effected in the plane of a cross-sectional slice of the body which intersects the patient's heart. The patient is located so that the heart is substantially at the center of the scanning movements. The lateral movements are substantially sinusoidal, arranged so that a substantially linear portion of the movement occurs when the source irradiates the heart, and the rotational movement is continuous or substantially continuous and any pauses are only brief, and during alternate lateral scans when the aforementioned substantially linear portions of movement occur. The scanning movements are synchronized to the patient's heart beats so that the heart is irradiated during a quiescent phase of its movement.

3 Claims, 4 Drawing Figures

RADIOGRAPHY

The present invention relates to radiography, and it relates especially to that branch of radiography which has become known as computerised tomography.

Computerised tomography involves scanning a source of radiation relative to the body of a patient under examination so as to project the radiation through a cross-sectional slice of the body along many substantially linear beam paths, some of which intersect within the body, detecting the radiation emergent from the body along each beam path, producing absorption signals indicative of the absorption suffered by the radiation on traversing the body along each beam path, and processing the absorption signals to evaluate the absorption (or transmission) coefficient, with respect to the radiation, at each of many elemental locations distributed over the slice. It is usual to display the evaluated coefficients as a visual representation, for example, as a cathode ray tube display which can be photographed or as a print-out of the actual absorption values.

U.S. Pat. No. 3,778,614 describes a number of examples of forms which computerised tomographic apparatus can take, and also claims such apparatus and methods of performing computerised tomography.

Computerised tomography has proved to be a useful diagnostic tool and has been usefully applied to many different parts of the human anatomy. Difficulty is experienced, however, in investigating cross-sectional body slices which intersect, or pass adjacent, the patient's heart. The motion of the heart is rapid in relation to the time taken to scan the source of radiation around the body to acquire the necessary absorption signals, and thus artefacts can be produced in the evaluated absorption values.

Application of computerised tomography to regions including the patient's heart, as well as to examination of the heart itself is clearly desirable, and U.S. Pat. No. 3,952,201 discloses and claims arrangements by means of which the acquisition of absorption values can be controlled in relation to a patient's heartbeats. The particular embodiment of computerised tomographic apparatus illustrated (by way of example only) in said U.S. Pat. No. 3,952,201 utilises a source of a wide, fan-shaped distribution of X-rays which simultaneously projects radiation along a large number of the aforementioned beam paths and an array of detectors devices disposed to receive the radiation emergent from the body along each of the simultaneously irradiated beam paths. The other beam paths are irradiated by rotating the source around the body slice under examination. In the example described, the detector array rotates with the source to maintain its alignment therewith.

Another form of scanning is that described and claimed in U.S. Pat. No. 3,946,234. The source generates a relatively narrow fan-shaped distribution of X-radiation and this is projected towards a small array of detectors. The source and the array are alternately swept laterally across the body and rotated through an angular step around the body. The angular steps take account of the fan angle. This form of scanning is known as traverse-and-rotate scanning, and has been adopted in the EMI-Scanner computerised tomographic apparatus CT5005 produced by EMI Medical Ltd, and it has been proposed, in U.S. Pat. No. 4,126,785 to synchronise such traverse-and-rotate scanning with a patient's heart beat so as to avoid, or at least reduce, the formation of the aforementioned artefacts.

This invention is concerned with providing computerised tomographic apparatus utilising a modified form of traverse-and-rotate scanning, in which there is considerable overlap between the lateral and rotational scanning movements, and in which no more than brief pauses in the rotational movement occur, in which apparatus the scanning movements are synchronised to the patient's heartbeats so that any brief pauses in the rotational movement occur while the heart is in a quiescent phase of its movement and the source and detector array are aligned with the heart.

According to the invention there is provided medical radiographic apparatus comprising a source of a substantially planar spread of x-radiation, the radiation projecting across an aperture, and diverging from said source as it proceeds across said aperture, detector means including a plurality of collimated x-radiation sensitive detector devices distributed across the spread and located at the opposite side of said aperture to said source, scanning means causing said source and said detector devices to execute, in synchronism, lateral scanning movements across, and rotational scanning motion around, said aperture, thus exposing a substantially planar region of said aperture to said x-radiation from many different locations relative thereto, means locating a patient's body with a cross-sectional slice thereof which passes through or near the patient's heart lying in said region, means monitoring the patient's heart beats and providing electrical signals indicative thereof, and means, controlling said scanning means in response to said electrical signals, causing said lateral scanning movements to occur substantially sinusoidally with time, one complete lateral scan to-and-fro across the aperture being executed for each heart beat, so that substantially linear parts of said sinusoidal lateral scanning movements in one direction only occur when radiation projects through the patient's heart.

Figure 2:
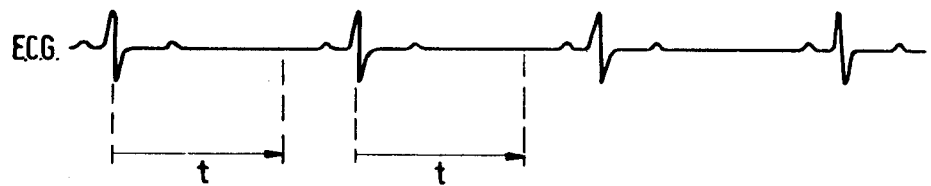
Figure 3:
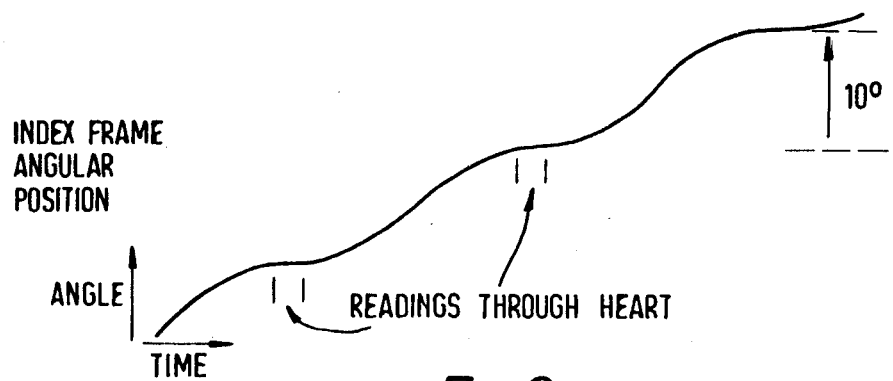
Figure 4:
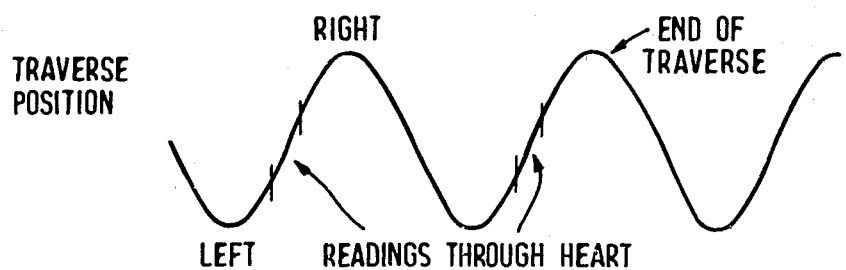

In order that the invention may be clearly understood and readily carried into effect, one embodiment thereof will now be described, by way of example only, with reference to the accompanying drawings, of which:

FIG. 1 shows, in schematic plan view, a traverse-and-rotate scanner modified to operate in accordance with one example of the invention, FIG. 2 shows a typical e.c.g. waveform, FIG. 3 shows, in graphic form, an indication of part of the rotational movement performed by the apparatus shown in FIG. 1, and FIG. 4 shows, in graphic form, an indication of the lateral movement performed by the apparatus shown in FIG. 1.

Referring now to FIG. 1, there is shown a CAT apparatus which is generally similar to that described and claimed in U.S. Pat. No. 3,946,234, but is modified in order to render it capable of being synchronised to heart movements. A turntable member 1 having a central aperture 2, to accommodate a body 3 to be examined, is mounted vertically for rotation about an axis 4 which is disposed centrally of the aperture 2. The member 1 is supported on three rotatable bearings 5, 6 and 7 which are journalled in a main frame 8 for the apparatus. The frame 8 remains stationary, being rigidly secured to a pedestal 9, and can take any suitable form, although it must of course be formed with an aperture coincident with the aperture 2.

The member 1 can be rotated in angular steps of (in this example) ten degrees by means of a Geneva mechanism generally shown at 10. The periphery of member 1 is formed with suitable prongs such as 11 which cooperate with pegs 12 and 13 on a continuously rotated disc 14 to effect the required step-wise rotary movement with only brief pauses between angular movements. A strong brake (not shown) is provided to effectively lock the member 1 in its angular position so long as neither of the pegs 12 or 13 is urging the member 1 to rotate. Disc 14 is journalled in the main frame 8 and is driven by an electric motor which is not shown. In apparatus in accordance with this example of the present invention said electric motor is a variable speed motor.

Mounted upon the turntable 1, and capable of performing a reciprocating lateral scanning motion relative thereto, is a lightweight but rigid scanning yoke 16. Yoke 16 can move on linear runners 17 and 18 which are fixedly mounted on the rotatable member 1 and are disposed chordally thereof. The lateral scanning motion is imparted to the yoke 16 by virtue of a toothed belt 19, which is stretched between a pair of toothed rollers 20 and 21 journalled in respective brackets (not shown) secured to the member 1, and to which belt the yoke 16 is attached by means of a bracket (not shown). The roller 20 is merely an idler roller, but roller 21 is driven by a variable speed reciprocating motor 22 which is attached by a strap-like bracket 23 to the member 1.

It will be appreciated that the pedestal 9 will be supported on a suitable girder or the like which ensures ground clearance of the yoke 16 in all angular positions of the turntable 1 and all lateral positions of the yoke 16 thereon.

A counter-balance weight 24 is secured to the opposite run of belt 19 to the yoke 16 and thus moves in opposition thereto to compensate for out-of-balance forces which would otherwise be set up by the lateral scanning motion of the yoke 16 and its attachments, which will now be described.

Attached to the yoke 16 is a source 25 of penetrating radiation, in this example X-radiation. The radiation is collimated to form a planar, fan-shaped beam, emanating from an effective point source. On the opposite side of yoke 16, with respect to the aperture 2, to the source 25 is an array 26 of thirty detectors sensitive to the radiation generated by the source 25, each viewing the source through a respective collimator; the collimators being disposed in a bank 27. In this example, neighbouring collimators are inclined to each other at an angle of $\frac{1}{3}°$ and since there are thirty detectors, this means that the angular spread of the beam of X-rays generated by the source 25 is 10°.

The body 3 is supported on a bed 28 and is secured thereon by means of straps each as 29. Gaps between the body and the fed are filled with a suitable packing material 30 which preferably absorbs the X-radiation to substantially the same extent as does human tissue. The material 30 is preferably contained in one or more plastic bags. The bed 28 is supported by legs 31 which stand on the pedestal 9.

It will be evident that the stepped, rotational scanning motion imparted by the Geneva mechanism 10 to the member 1 needs to be synchronised with the lateral scanning motion imparted to the yoke 16 by the reciprocating motor 22 and, to this end, the disc 14 is formed with an annular graticule 32, and a fixed photodetector 33 is provided, together with a suitable light source (not shown) to provide timing pulses indicative of the passage of markings on the graticule 32 past the photodetector 33. Thus the rotational scanning motion can be monitored, and similarly a linear graticule 34 is fixedly attached to the yoke 16 and cooperates with a second photodetector 35, which is mounted on the member 1 so as to rotate therewith, and a similarly mounted light source (not shown) to produce timing pulses indicative of the progress of the lateral scanning. Both graticules 32 and 34 comprise translucent or transparent members bearing regularly spaced opaque lines printed, etched or otherwise provided thereon.

It will be observed that the control system for the driving motor for disc 14 consists of an e.c.g. sensor 37, a pulse shaper 38, a control circuit 39 and a position-sensitive feedback connection 36 from graticule 32 and photocell unit 33 to the control circuit 39. This ensures that the disc 14 rotates continuously at a rate determined by the patient's heartbeats.

The motor 22, on the other hand, is required to drive the yoke 16 and its attachments to and fro relative to the aperture 2 in a substantially sinusoidal manner with the substantially linear portions of the sinusoidal motion occurring in the centre of each lateral traverse. In order to achieve this, the disc 14 may be formed with a second graticule (not shown) having markings which exhibit sinusoidal variations in spacing (unlike the regularly spaced markings of graticule 32). A photocell unit 40 is provided to co-operate with the aforementioned second graticule to generate suitable sinusoidally varying timing pulses indicative of the desired lateral position of the yoke 16. These pulses are differentiated in a conventional differentiating circuit 41 to produce signals indicative of transverse velocity of the yoke 16 and these signals are applied to a second control circuit 42 which controls the motor 22. A feedback control loop is provided from a tacho generator (not shown) of conventional kind, coupled to the motor 22, to the control circuit 42. Instead of using a second graticule on disc 14, together with the associated photocell unit 40, the signals derived from the photocell unit 33 could be applied to a sinusoidal function generator of known kind. In any event, to aid control of the sinusoidal lateral velocity, buffer springs (not shown) which usually are provided to engage with the source 25 and the counterbalance weight 24 when they reach the ends of their lateral traverses, can be lengthened so that both components 24 and 25 are under the control of one spring or the other throughout the lateral movement.

An additional control on the lateral position of the yoke can be obtained, if desired, by feeding the signals from the photocell unit 33 and from the photocell unit 35 to a position checking circuit 43, the output of which is applied to the control circuit 42. For this purpose, only the signals derived from the photocell unit 35 at or adjacent the centre of each lateral scan need be applied to the circuit 43, but the timing signals derived from unit 35 are also required for another purpose, as will be described presently, so it is not possible to use a shorter graticule in place of the graticule 34.

Each detector in the array 26 feeds, in known manner, a respective pre-processing circuit 44 only one of which is shown in the drawing. Each pre-processing circuit 44 includes an amplifier 45, a resettable integrator 46, which is read and reset at least one hundred and sixty times, by the timing pulses produced by the photocell unit 35, during each lateral traverse of the yoke 16 across the aperture 2, an analogue-to-digital converter circuit 47 and a log converter circuit 48.

All of the pre-processing circuits such as 44 feed a processing circuit 49 which preferably takes one of the forms described and claimed in U.S. Pat. No. 3,924,129 but can alternatively take any other convenient form. The circuit 49 is effective to evaluate the aforementioned absorption (or transmission) coefficients at each of many elemental locations distributed over a cross-sectional slice of the patient's body disposed in the aperture 2. The evaluated coefficients are displayed at 50 in any convenient manner.

The apparatus described hitherto operates in the manner now to be described, and basically it will be seen that, instead of executing alternate lateral traverses and angular steps around the patient, the X-ray source 25 and the detector array 26 execute a motion such that the angular steps are almost contiguous and that the brief dwell periods between successive angular steps are timed to occur when the yoke is in a central region of its linear traverses and at a fixed time after each heartbeat. The to and fro, or lateral scanning movement, of the yoke 16 is substantially continuous.

Referring now to FIGS. 2 to 4, FIG. 2 shows, in schematic form, a waveform derived from the e.c.g. sensor 37, and indicates a period t following each heartbeat which corresponds to a quiescent period of the heart's motion and indicates the point at which the centre of the lateral scan and the centre of the brief dwell period between two successive rotational steps are desired to occur. It is assumed, of course, that the patient is positioned so that his heart is substantially at the centre of the aperture 2.

FIGS. 3 and 4 show, respectively, variation of the angle of turntable member 1 with time and the variation with time of the position of source 25 and detector array 26 relative to the ends of guide 17.

From FIG. 3 it will be seen that the member 1 is in motion for about 90% of each cycle of operation and that the 10% of the time when it is stationary is timed to exactly straddle the time t. From FIG. 4 it will be seen that the source 25 and detector array 26 execute a sinusoidal motion, the substantially linear portions of the left-to-right movements of which are timed to coincide with the periods when turntable member 1 is stationary. It is at the periods when turntable 1 is stationary that the source 25 and detector array 26 are effecting the central part of each traverse from left to right (i.e. from idler wheel 20 towards the driven wheel 21) and at these times absorption data relating to the heart is obtained, because the patient has been appropriately located in the aperture. It will be noted that heart absorption data are only obtained during lateral scan when the source 25 is moving away from wheel 20 and towards wheel 21. On the return movement, the source 25 is blanked off and no data is collected. This is done to reduce possible errors due to phase shift across the heart if data were collected on all lateral scans.

The fact that absorption data is also collected during those parts of active lateral scans effected when the member 1 is not stationary will give rise to some distortion of the evaluation of coefficients in regions of the body slice away from the heart, but this distortion is of little consequence.

The present invention permits scanning to be effected with heart rates as high as 120 beats per minute, and a scan of a patient with such a heart rate can be effected in only ten seconds.

In summary then, in the specific embodiment described, the lateral scanning movements and rotational scanning movements executed by the source 25 (and the detectors 26) overlap to a substantial extent, the lateral movements being sinusoidal, or substantially so. It is well known that certain parts of a sinusoidal movement can be regarded as substantially linear and thus, during each lateral scan in either direction there is a period, straddling the centre of the scan, when the scanning is substantially linear. The fan of radiation produced by the source 25 subtends an angle of 10° and the rotational movement is effected in 10° steps. The rotation, however, is substantially continuous, dwelling only briefly during alternate periods of substantially linear lateral scanning. The patient is located so that at the times of occurrence of the brief dwells in the rotational movement, the x-radiation is sweeping the patient's heart; the scanning being synchronised to the patient's heart beats and the timing device being such that the x-radiation sweeps across the patient's heart while it is quiescent.

Although the invention has been described in terms of the preferred embodiment of a stepped rotation with a dwell period when the radiation is projected through the patient's heart, it is possible to use a system having a continuous rotation. For the example given hereinbefore, this should rotate accurately through 10° for one forward and backward movement of the lateral scanning movement. The motions can be provided and synchronised by driving the lateral scan from a simple crank on the rotation motor instead of the 'Geneva' mechanism.

It will be understood that the continuous rotation will cause the radiation paths passing through the patient's heart to be fan distributed. It is, however, known that data for radiation paths which are distributed in this way can be processed by a circuit as described and claimed in the said U.S. Pat. No. 3,924,129 with appropriate amendments to the procedure. This is described for example, in U.S. Pat. No. 4,010,371.

What we claim is:

1. A computerized tomographic scanner for examining cross-sectional slices of the bodies of patients, the scanner including means defining a patient position, source means arranged to project a divergent spread of penetrating radiation across said patient position, an array of radiation-sensitive detectors, aligned with said spread, for detecting radiation emergent from said patient position, scanning means causing said source means and said detectors to execute traversing movements across and rotating movements around said patient position, sensing means for sensing motion of a patient's heart and for producing electrical signals indicative of such motion, and control means, responsive to said electrical signals, for controlling the traversing and rotating scanning movements and causing, a predetermined time t after each heartbeat, an interruption in the rotating movement to occur coincidentally with a central portion of the traversing movement; said control means causing: said rotating movement to proceed smoothly, apart from said interruptions, said traversing movements to be regularly reciprocating bi-directional movements and said interruptions in said rotating movement to occur during traversing movements in one only of the two directions; the patient's body being positioned so that the heart is irradiated only when said interruptions occur.

2. A scanner according to claim 1 including means for deriving electrical output signals from said detectors during traversing movements in said one direction only, the radiation being suppressed during traversing movements in the other direction.

3. A scanner according to claim 2 including means for processing said electrical output signals derived from said detectors to produce a representation of the variation of x-ray absorption with position over a cross-sectional slice of the patient's body.

* * * * *